United States Patent [19]
Desch

[11] Patent Number: 6,050,957
[45] Date of Patent: Apr. 18, 2000

[54] MULTIPLE-DRAW, VARIABLE SUCTION SYRINGE

[76] Inventor: Larry W. Desch, 8247 W. 141st St., Orland Park, Ill. 60462

[21] Appl. No.: 09/108,444

[22] Filed: Jul. 1, 1998

[51] Int. Cl.[7] .................................................. A61B 10/00
[52] U.S. Cl. ........................... 600/579; 604/181; 604/218
[58] Field of Search ...................................... 600/575, 576, 600/578, 579; 604/110, 195, 181, 182, 192, 197, 198, 220, 225, 226, 263

[56] References Cited

U.S. PATENT DOCUMENTS

| | | |
|---|---|---|
| 3,557,778 | 1/1971 | Hughes . |
| 3,620,418 | 11/1971 | Stevens et al. . |
| 3,957,052 | 5/1976 | Topham . |
| 4,210,173 | 7/1980 | Choksi et al. . |
| 4,447,235 | 5/1984 | Clarke . |
| 4,732,162 | 3/1988 | Martell . |
| 5,147,329 | 9/1992 | Brannon . |
| 5,518,005 | 5/1996 | Brannon . |

*Primary Examiner*—Max Hindenburg
*Assistant Examiner*—Pamela L. Wingood
*Attorney, Agent, or Firm*—Robert Toczycki

[57] ABSTRACT

A multiple-draw syringe for extraction of a fluid into at least one fluid container comprising a cylindrical body having a distal end and an open proximal end, a hollow needle extending from the distal end, a piston sealably engaging and slidable along an interior wall of the cylindrical body, a ball check valve, a plunger for moving the piston proximally or distally within the cylindrical body, and a conduit extending through the piston to an enclosed fluid collection receptacle. The distal end includes a first chamber provided with a fluid inlet at one end and a fluid outlet at an opposite end. The first chamber has a conical sidewall adjacent the fluid inlet and a plurality of radially spaced stems adjacent the fluid outlet. The distal end is open to the flow of a fluid into the cylindrical body through the first chamber when the syringe is in use. The piston includes a piston face extending transversely across the interior wall and defines a fluid chamber between the piston face and the distal end of the cylindrical body. The ball check valve is positioned in the first chamber to permit flow of fluid through the first chamber in one direction only. The plunger is attached at one end to the piston and has another end extending beyond the open proximal end of the cylindrical body. The conduit has a sufficiently narrow, uniform internal diameter to induce the passage of a fluid from the fluid chamber through the conduit and into the enclosed fluid collection receptacle.

12 Claims, 3 Drawing Sheets

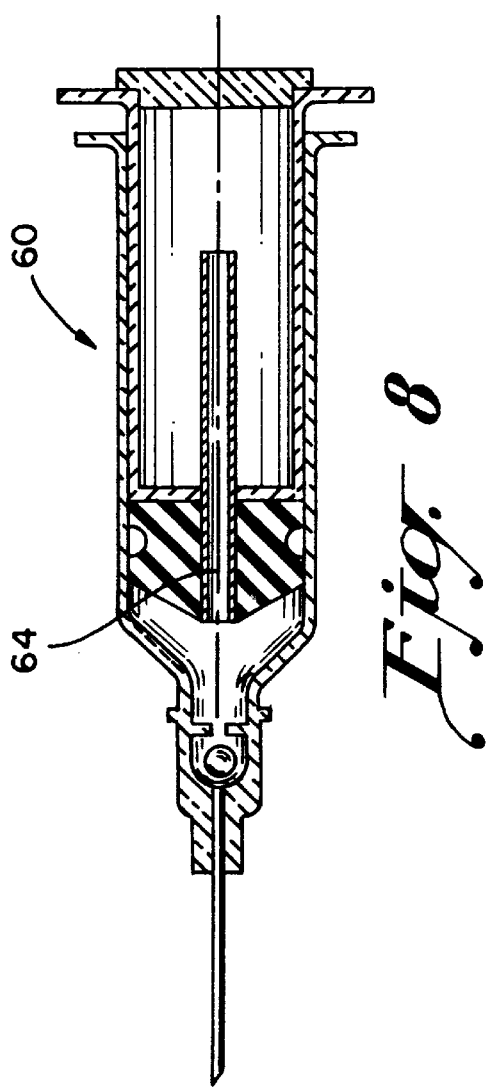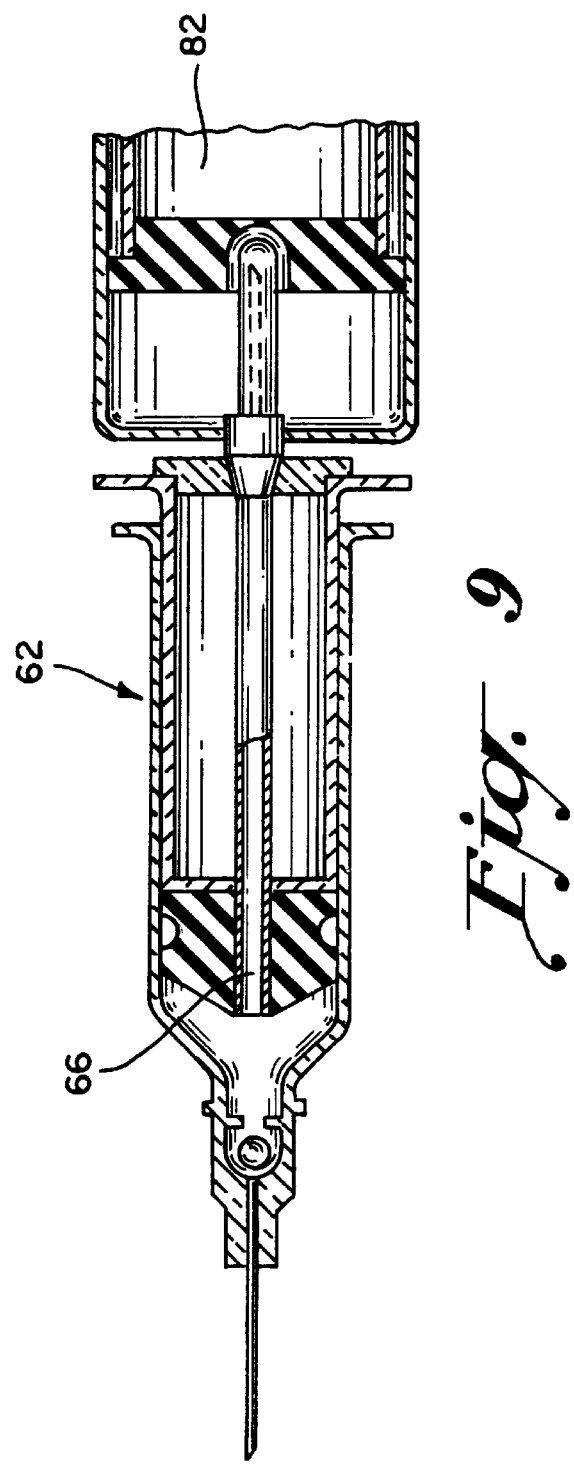

MULTIPLE-DRAW, VARIABLE SUCTION SYRINGE

BACKGROUND OF THE INVENTION

1. Field of the Invention

The present invention relates generally to a new and improved syringe for drawing blood that helps to address the problem of drawing blood from patients who have small veins or veins which collapse. Many of these patients are children who may not be entirely cooperative during blood drawing procedures. Therefore, my new and improved syringe allows for blood to be drawn into multiple tubes without removing the needle from the vein. In addition, the syringe also minimizes the risk to the person doing the venipuncture for accidental "needle sticks" and exposure to infectious diseases. The present invention also provides a check valve within the syringe to prevent return of drawn blood or backflow of testing solutions (chemicals) into the bloodstream of the patient.

2. Description of the Prior Art

Over the past few years, especially since AIDS has been described, there has been a number of changes to the basic design of syringes and needles in an attempt to minimize accidental "needle sticks" and the possible transfer of infectious agents. Most of these designs have focused on ways to automatically sheath the needle after the blood is drawn.

In addition, over the past decade, there have been methods developed to facilitate the way in which multiple tubes of blood can be collected following a single venipuncture. Primarily this has been done by the use of a system involving Vacutainer® tubes which, unfortunately, tend to collapse small or weak-walled veins because of the vacuum being applied to the veins.

Other types of syringes that could allow for multiple tubes of blood include syringes with three-way stopcocks coupled to syringes in order to do venipuncture in such a way that appropriate suction could be applied to pull out blood from a vein without collapsing it. During the venipuncture procedure, by intermittently switching the valve on the stopcock, multiple sample tubes could be filled. This technique, however, is much less the satisfactory because of all the movement involved which would usually cause the needle to come out of the vein, especially in a patient who was not completely motionless.

As blood is drawn from a patient with weak or small veins, the punctured vein may begin to collapse. At that point it is common to stop pulling on the plunger of the syringe and possibly even push the plunger partially back into the syringe to try and keep the vein from collapsing, however, this technique is not possible if the syringe already contains a solution, such as a testing solution, since this solution can cause serious damage or even death to the patient. It is therefore desirable to provide a syringe that can also prohibit the backflow of drawn blood back into the vein of a patient.

Certain U.S. patents are peripherally related to the problem, but none show the structural promise needed for an instrument usable in the wide area of applications addressed herein. These prior approaches are given representatively in the following Topham U.S. Pat. No. 3,957,052; Hughes U.S. Pat. No. 3,557,778; and Brannon U.S. Pat. No. 5,147,329.

There have been various types of syringes developed and made available in the marketplace, but none have been able to provide for an inexpensive multiple-draw, variable suction syringe as is disclosed herein. Furthermore, none of the prior art syringes provide for a syringe that addresses the problem of drawing blood from patients who have small veins or veins that easily collapse, that can allow for easy withdrawal of multiple tubes of blood, and that allow for a minimal amount of "needle sticks". Other types of syringes disclosed in the prior art do not offer the flexibility and inventive features of my convenient and easy-to-use syringe. As will be described in greater detail hereinafter, the multiple-draw, variable suction syringe of the present invention differs significantly from those previously proposed.

SUMMARY OF THE INVENTION

According to my present invention I have provided a multiple-draw, variable suction syringe for extraction of a fluid into at least one fluid container comprising a cylindrical body having a distal end and an open proximal end, a hollow needle extending from the distal end, a piston sealably engaging and slidable along an interior wall of the cylindrical body, a check valve, a plunger for moving the piston proximally or distally within the cylindrical body, and a conduit extending through the piston to an enclosed fluid collection receptacle. The distal end includes a first chamber provided with a fluid inlet at one end and a fluid outlet at an opposite end. The first chamber has a conical sidewall adjacent the fluid inlet and a plurality of radially spaced stems adjacent the fluid outlet. The distal end is open to the flow of a fluid into the cylindrical body through the first chamber when the syringe is in use. The hollow needle is in fluid communication with the first chamber through the fluid inlet. The piston includes a piston face extending transversely across the interior wall and defines a fluid chamber between the piston face and the distal end of the cylindrical body. The check valve is positioned in the first chamber to permit flow of fluid through the first chamber in one direction only. The check valve includes a ball larger in diameter than the fluid inlet and is shiftable from a position in engagement with the conical sidewall whereby to close the fluid inlet and a position supported by the stems in spaced relationship from the fluid outlet whereby to permit flow of fluid through the first chamber, out of the fluid outlet and into the fluid chamber. The plunger is attached at one end to the piston and has another end extending beyond the open proximal end of the cylindrical body. The plunger has a size and shape that minimizes substantial lateral motion in the cylindrical body. The conduit has a sufficiently narrow, uniform internal diameter to induce the passage of a fluid from the fluid chamber through the conduit and into the enclosed fluid collection receptacle.

According to other features in the invention I have provided an improved multiple-draw, variable suction syringe as described above wherein the conduit further includes a conduit chamber provided with a conduit inlet at one end and a conduit outlet at the opposite end. The conduit chamber has a conduit conical sidewall adjacent the conduit inlet and a plurality of radially spaced stems adjacent the conduit outlet. The conduit inlet is open to the flow of a fluid into the enclosed fluid collection receptacle through the conduit chamber when the syringe is in use. A second check valve is positioned in the conduit chamber to permit flow of fluid through the conduit chamber in one direction only. The second check valve includes a ball larger in diameter than the conduit inlet and is shiftable from a position in engagement with the conduit conical sidewall whereby to close the conduit inlet and a position supported by the stems in spaced relationship from the conduit outlet whereby to permit flow of fluid through the conduit chamber, out of the conduit outlet and into the enclosed fluid collection receptacle.

Another feature of my invention relates to the multiple-draw syringe as described above, wherein the enclosed fluid collection receptacle is detachably engaged with the conduit, whereby multiple fluid collection receptacles can be used to obtain multiple blood samples from one needle venipuncture.

Yet other features relate to the multiple-draw syringe as described above, wherein the hollow needle is detachably engaged with the distal end of the cylindrical body.

Other objects, features and advantages of my invention will become more readily apparent upon reference to the following description when taken in conjunction with the accompanying drawings, which drawings illustrate several embodiments of my invention.

DESCRIPTION OF THE DRAWINGS

FIG. 3 is a sectional side view of my syringe illustrating blood flow while the plunger is pushed in;

FIG. 8 is a sectional side view illustrating still a further embodiment of my syringe; and FIG. 9 is a partial sectional side view illustrating yet another embodiment of my syringe wherein multiple blood samples can be taken.

DETAILED DESCRIPTION OF THE PREFERRED EMBODIMENT

Figure 1:
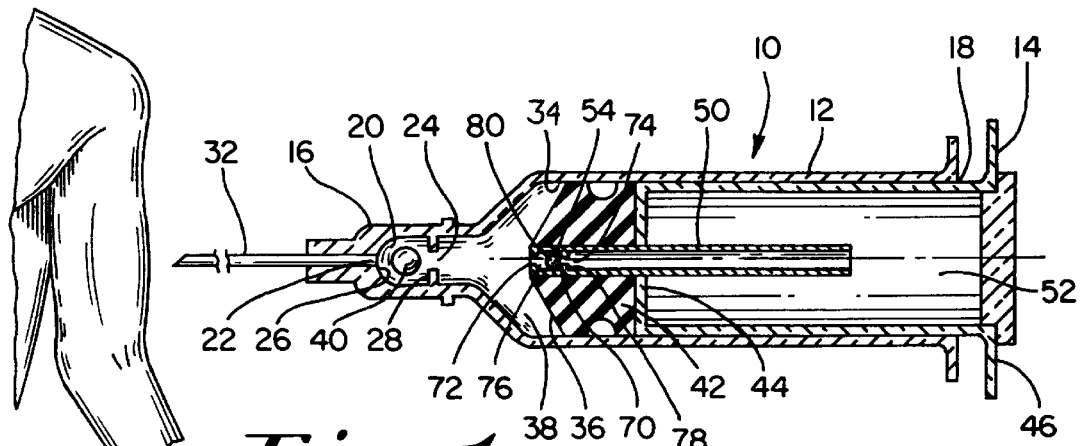
FIG. 1 is a sectional side view of my syringe in accordance with important features of my invention.
Figure 2:
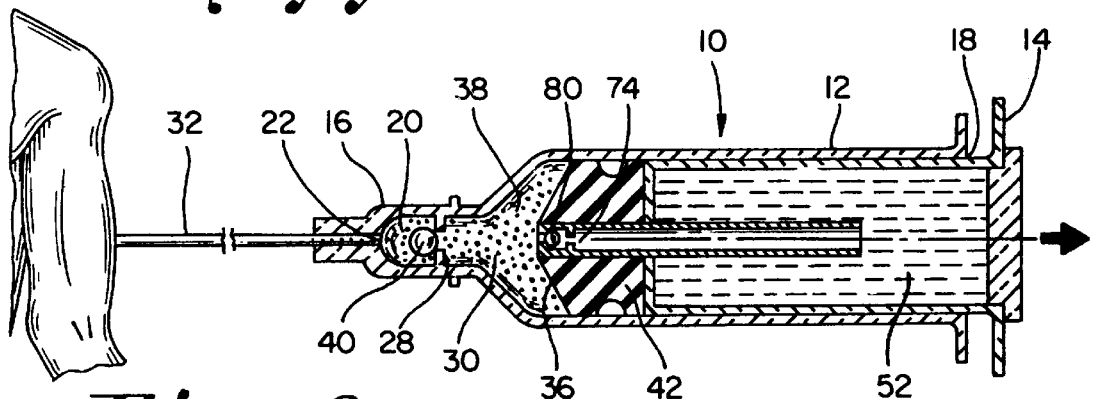
FIG. 2 is a sectional side view of my syringe with first obtained fluid within the cylindrical body of the syringe while the plunger is pulled.
Figure 3:
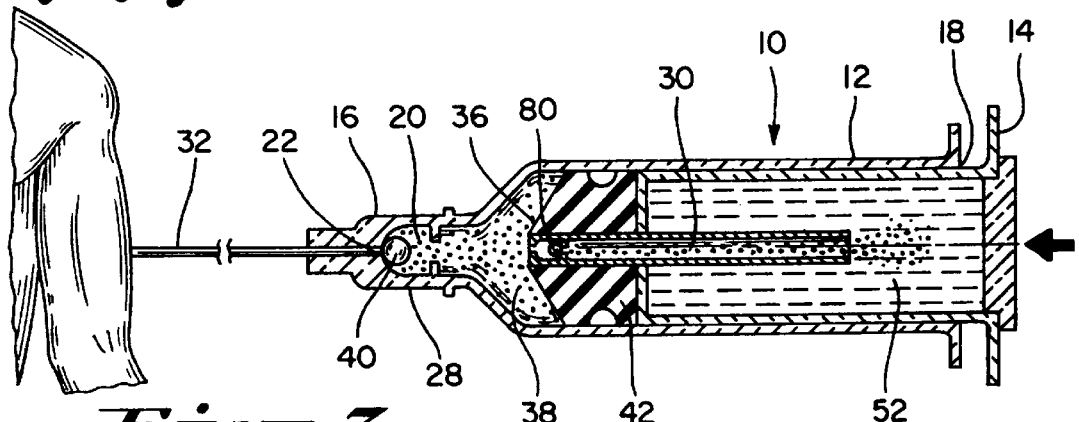

Referring now to the drawings, FIGS. 1–3 show my new and improved syringe 10 which includes a cylindrical body 12, and a piston 14. The cylindrical body 12 has a distal end 16 and an open proximal end 18. The distal end 16 of the syringe includes a first chamber 20 provided with a fluid inlet 22 at one end and a fluid outlet 24 at an opposite end (FIGS. 1–3, 5).

The first chamber 20 has a conical sidewall 26 adjacent the fluid inlet 22 and a plurality of radially spaced stems 28 adjacent the fluid outlet 24. The distal end 16 is open to the flow of a fluid 30 into the cylindrical body 12 through the first chamber 20 when the syringe is in use.

A hollow needle 32 extends from the distal end 16 of the cylindrical body 12 and in fluid communication with the first chamber 20 through the fluid inlet 22. The piston 14 is sealably engaged and is slidable along an interior wall 34 of the cylindrical body 12. The piston 14 includes a piston face 36 extending transversely across the interior wall 12 and defines a fluid chamber 38 between the piston face 36 and the distal end 16 of the cylindrical body 12.

A check valve is positioned in the first chamber 20 to permit flow of fluid through the first chamber in one direction only. The check valve includes a ball 40 larger in diameter than the fluid inlet 22 and is shiftable from a position in engagement with the conical sidewall 26 whereby to close the fluid inlet 22 and a position supported by the stems 28 (FIG. 4) in spaced relationship from the fluid outlet 24 whereby to permit flow of fluid through the first chamber 20, out of the fluid outlet 24 and into the fluid chamber 38.

A plunger 42 is attached at the end 44 of the piston 18 and moves with the piston proximally or distally within the cylindrical body 12. The plunger 42 has another end 46 extending beyond the open proximal end 18 of the cylindrical body 12. The plunger 42 has a size and shape that minimizes substantial lateral motion within the cylindrical body.

A conduit 50 extends through the piston 14 to an enclosed fluid collection receptacle 52. The conduit 50 has a sufficiently narrow, uniform internal diameter to induce the passage of a fluid from the fluid chamber 38 through the conduit 50 and into the enclosed fluid collection receptacle 52.

The multiple-draw syringe can also optionally include another check valve 54 positioned within the conduit 50 of the piston 14. This additional check valve 54 works better with people who have extremely weak veins, however, a syringe 60, 62 (FIGS. 8 and 9) without the additional check valve positioned within the conduit 64, 66 still works well with weak veins and provides advantage above and beyond the syringes disclosed in the prior art.

Figure 4:
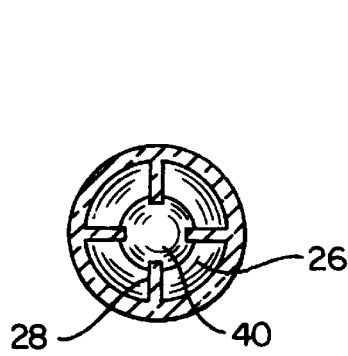
FIG. 4 is sectional end view illustrating the ball check valve within my syringe, as taken along lines 4—4 in FIG. 5.
Figure 5:
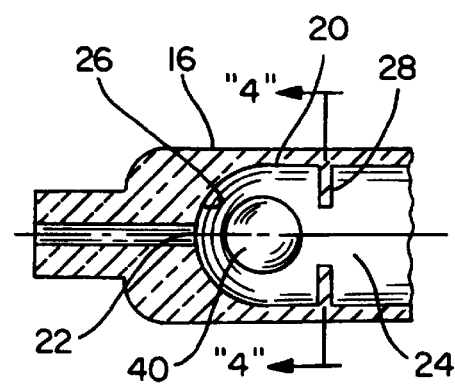
FIG. 5 is an enlarged partial sectional side view showing the ball check valve in my syringe.

Referring back to FIGS. 1–3, the conduit 50 includes a conduit chamber 70 provided with a conduit inlet 72 at one end and a conduit outlet 74 at the opposite end (similarly as seen in FIGS. 4 and 5). The conduit chamber 70 has a conduit conical sidewall 76 adjacent the conduit inlet 72 and a plurality of radially spaced stems 78 adjacent the conduit outlet 74. The conduit inlet 72 is open to the flow of a fluid 30 into the enclosed fluid collection receptacle 52 through the conduit chamber 70 when the syringe is in use. A second check valve is positioned in the conduit chamber 70 to permit flow of fluid through the conduit chamber in one direction only. The second check valve including a ball 80 larger in diameter than the conduit inlet 72 and is shiftable from a position in engagement with the conduit conical sidewall 76 whereby to close the conduit inlet, and a position supported by the stems 78 in spaced relationship from the conduit outlet 74 whereby to permit flow of fluid through the conduit chamber 70, out of the conduit outlet and into the enclosed fluid collection receptacle 52.

The multiple-draw syringe of the present invention can provide for an enclosed fluid collection receptacle 82 (FIG. 9) that is detachably engaged with the conduit 66, whereby multiple fluid collection receptacles can be used to obtain multiple blood samples from one needle venipuncture. This version may also make use of the second check valve assembly positioned within the plunger, as shown in FIGS. 1–3.

Figure 6:
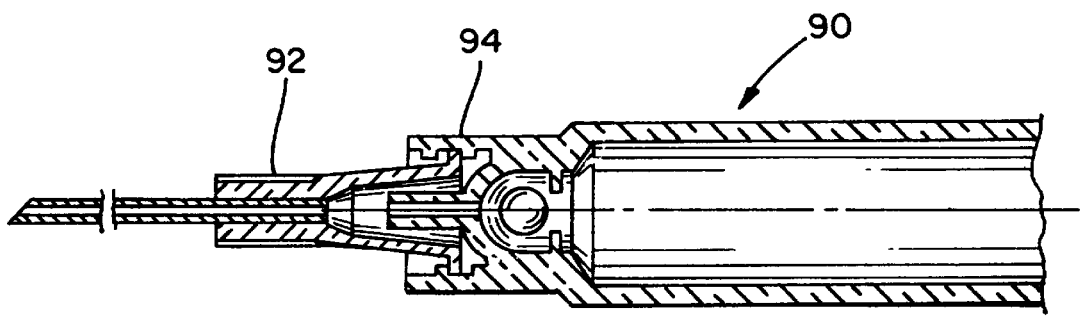
FIG. 6 is a sectional side view illustrating another embodiment of my syringe.

The multiple-draw syringe of the present invention is also adaptable to accept standard needles. FIG. 6 illustrates a syringe 90 of the present invention, wherein the hollow needle assembly 92 is detachably engaged with the distal end 94 of the syringe.

Figure 7:
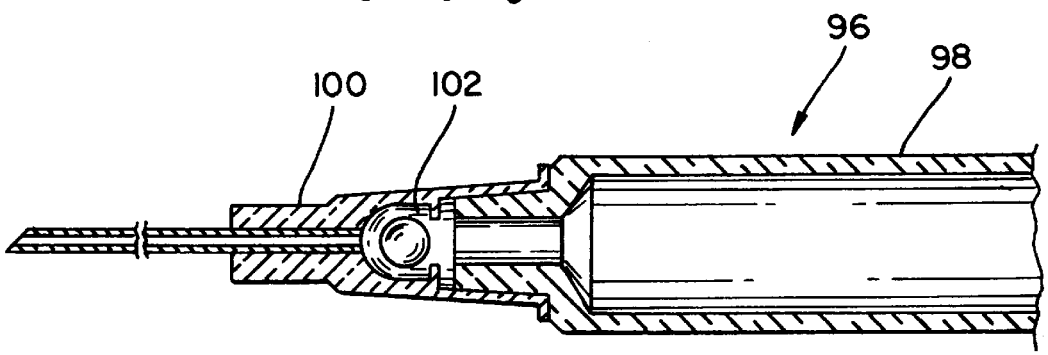
FIG. 7 is a sectional side view illustrating yet another embodiment of my syringe.

FIG. 7 further illustrates a syringe 96 that utilizes a standard cylindrical syringe body 98 with a hollow needle assembly or detachable chamber 100 having a ball check valve 102 located within the hollow needle assembly or detachable chamber 100. The different versions shown in FIGS. 6 and 7 illustrate how different versions of my syringe could be made and take into consideration ease of use, adaptability, and manufacturing costs. These versions shown in FIGS. 6 and 7 are intended to be used with a plunger similar to the ones shown in FIGS. 1–3, 8 and 9.

As various possible embodiments may be made in the above invention for use for different purposes and as various changes might be made in the embodiments and method above set forth, it is understood that all of the above matters here set forth or shown in the accompanying drawings are to be interpreted as illustrative and not in a limiting sense.

I claim:

1. A multiple-draw syringe for extraction of a fluid into at least one fluid container comprising:

a cylindrical body having a distal end and an open proximal end, said distal end including a first chamber provided with a fluid inlet at one end and a fluid outlet at an opposite end, said first chamber having a conical sidewall adjacent said fluid inlet and a plurality of radially spaced stems adjacent said fluid outlet, said distal end being open to the flow of a fluid into said cylindrical body through said first chamber when said syringe is in use;

a hollow needle extending from said distal end of the cylindrical body and in fluid communication with the first chamber through said fluid inlet;

a piston sealably engaging and slidable along an interior wall of said cylindrical body, said piston including a piston face extending transversely across said interior wall and defining a fluid chamber between said piston face and said distal end of said cylindrical body;

check valve means in said first chamber to permit flow of fluid through said first chamber in one direction only, said check valve means including a ball larger in diameter than said fluid inlet and shiftable from a position in engagement with said conical sidewall whereby to close said fluid inlet and a position supported by said stems in spaced relationship from said fluid outlet whereby to permit flow of fluid through said first chamber, out of said fluid outlet and into said fluid chamber;

plunger means for moving said piston proximally or distally within said cylindrical body, said plunger means being attached at one end to said piston, said plunger means having another end extending beyond said open proximal end of said cylindrical body, said plunger means having a size and shape that minimizes substantial lateral motion in said cylindrical body; and conduit means extending through said piston to an enclosed fluid collection receptacle, said conduit means having a sufficiently narrow, uniform internal diameter to induce the passage of a fluid from said fluid chamber through said conduit means and into said enclosed fluid collection receptacle, said conduit means further including a conduit chamber provided with a conduit inlet at one end and a conduit outlet at the opposite end, said conduit chamber having a conduit conical sidewall adjacent the conduit inlet and a plurality of radially spaced stems adjacent said conduit outlet, said conduit inlet being open to the flow of a fluid into said enclosed fluid collection receptacle through said conduit chamber when said syringe is in use, and a second check valve means in said conduit chamber to permit flow of fluid through said conduit chamber in one direction only, said second check valve means including a ball larger in diameter than said conduit inlet and shiftable from a position in engagement with said conduit conical sidewall whereby to close said conduit inlet and a position supported by said stems in spaced relationship from said conduit outlet whereby to permit flow of fluid through said conduit chamber, out of said conduit outlet and into said enclosed fluid collection receptacle.

2. The multiple-draw syringe of claim 1, wherein said enclosed fluid collection receptacle is detachably engaged with said conduit means, whereby multiple fluid collection receptacles can be used to obtain multiple blood samples from one needle venipuncture.

3. The multiple-draw syringe of claim 1, wherein said hollow needle is detachably engaged with said distal end of the cylindrical body.

4. A multiple-draw syringe for extraction of a fluid into at least one fluid container comprising:

a cylindrical body having a distal end and an open proximal end, said distal end having a detachable chamber provided with a fluid inlet at one end and a fluid outlet at an opposite end attached thereto, said detachable chamber having a conical sidewall adjacent said fluid inlet and a plurality of radially spaced stems adjacent said fluid outlet, said distal end being open to the flow of a fluid into said cylindrical body through said detachable chamber when said syringe is in use;

a hollow needle extending from said detachable chamber and in fluid communication with said fluid inlet;

a piston sealably engaging and slidable along an interior wall of said cylindrical body, said piston including a piston face extending transversely across said interior wall and defining a fluid chamber between said piston face and said distal end of said cylindrical body;

check valve means in said detachable chamber to permit flow of fluid through said first chamber in one direction only, said check valve means including a ball larger in diameter than said fluid inlet and shiftable from a position in engagement with said conical sidewall whereby to close said fluid inlet and a position supported by said stems in spaced relationship from said fluid outlet whereby to permit flow of fluid through said detachable chamber, out of said fluid outlet and into said fluid chamber;

plunger means for moving said piston proximally or distally within said cylindrical body, said plunger means being attached at one end to said piston, said plunger means having another end extending beyond said open proximal end of said cylindrical body, said plunger means having a size and shape that minimizes substantial lateral motion in said cylindrical body; and conduit means extending through said piston to an enclosed fluid collection receptacle, said conduit means having a sufficiently narrow, uniform internal diameter to induce the passage of a fluid from said fluid chamber through said conduit means and into said enclosed fluid collection receptacle, said conduit means further including a conduit chamber provided with a conduit inlet at one end and a conduit outlet at the opposite end, said conduit chamber having a conduit conical sidewall adjacent the conduit inlet and a plurality of radially spaced stems adjacent said conduit outlet, said conduit inlet being open to the flow of a fluid into said enclosed fluid collection receptacle through said conduit chamber when said syringe is in use, and a second check valve means in said conduit chamber to permit flow of fluid through said conduit chamber in one direction only, said check valve means including a ball larger in diameter than said conduit inlet and shiftable from a position in engagement with said conduit conical sidewall whereby to close said conduit inlet and a position supported by said stems in spaced relationship from said conduit outlet whereby to permit flow of fluid through said conduit chamber, out of said conduit outlet and into said enclosed fluid collection receptacle.

5. The multiple-draw syringe of claim 4, wherein said enclosed fluid collection receptacle is detachably engaged with said conduit means, whereby multiple fluid collection receptacles can be used to obtain multiple blood samples from one needle venipuncture.

6. The multiple-draw syringe of claim 4, wherein said hollow needle is detachably engaged with said distal end of the cylindrical body.

7. A multiple-draw syringe for extraction of a fluid into at least one fluid container comprising:

- a cylindrical body having a distal end and an open proximal end, said distal end including a first chamber provided with a fluid inlet at one end and a fluid outlet at an opposite end, said distal end being open to the flow of a fluid into said cylindrical body through said first chamber when said syringe is in use;
- a hollow needle extending from said distal end of the cylindrical body and in fluid communication with the first chamber through said fluid inlet;
- a piston sealably engaging and slidable along an interior wall of said cylindrical body, said piston including a piston face extending transversely across said interior wall and defining a fluid chamber between said piston face and said distal end of said cylindrical body;
- check valve means in said first chamber to permit flow of fluid through said first chamber in one direction only, whereby to permit flow of fluid through said first chamber, out of said fluid outlet and into said fluid chamber;
- plunger means for moving said piston proximally or distally within said cylindrical body, said plunger means being attached at one end to said piston, said plunger means having another end extending beyond said open proximal end of said cylindrical body, said plunger means having a size and shape that minimizes substantial lateral motion in said cylindrical body; and
- conduit means extending through said piston to an enclosed fluid collection receptacle, said conduit means having a sufficiently narrow, uniform internal diameter to induce the passage of a fluid from said fluid chamber through said conduit means and into said enclosed fluid collection receptacle, said conduit means further including a conduit chamber provided with a conduit inlet at one end and a conduit outlet at the opposite end, said conduit inlet being open to the flow of a fluid into said enclosed fluid collection receptacle through said conduit chamber when said syringe is in use, and a second check valve means in said conduit chamber to permit flow of fluid through said conduit chamber in one direction only, whereby to permit flow of fluid through said conduit chamber, out of said conduit outlet and into said enclosed fluid collection receptacle.

8. The multiple-draw syringe of claim 7, wherein said check valve means comprises a ball check valve.

9. The multiple-draw syringe of claim 7, wherein said first chamber has a conical sidewall adjacent said fluid inlet and a plurality of radially spaced stems adjacent said fluid outlet, said check valve means including a ball larger in diameter than said fluid inlet and shiftable from a position in engagement with said conical sidewall whereby to close said fluid inlet and a position supported by said stems in spaced relationship from said fluid outlet.

10. The multiple-draw syringe of claim 7, wherein said conduit chamber has a conduit conical sidewall adjacent the conduit inlet and a plurality of radially spaced stems adjacent said conduit outlet, said second check valve means including a ball larger in diameter than said conduit inlet and shiftable from a position in engagement with said conduit conical sidewall whereby to close said conduit inlet and a position supported by said stems in spaced relationship from said conduit outlet.

11. The multiple-draw syringe of claim 7, wherein said enclosed fluid collection receptacle is detachably engaged with said conduit means, whereby multiple fluid collection receptacles can be used to obtain multiple blood samples from one needle venipuncture.

12. The multiple-draw syringe of claim 7, wherein said hollow needle is detachably engaged with said distal end of the cylindrical body.

* * * * *